(12) United States Patent
Simon et al.

(10) Patent No.: US 7,045,116 B2
(45) Date of Patent: May 16, 2006

(54) TREATMENT OF OSTEOMYELITIS WITH RADIOPHARMACEUTICALS

(75) Inventors: Dana W. Simon, Angleton, TX (US); Alan D. Strickland, Lake Jackson, TX (US); Jaime Simon, Angleton, TX (US); Daniel J. Macey, Birmingham, AL (US); R. Keith Frank, Lake Jackson, TX (US); Kenneth McMillan, Richwood, TX (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/317,738

(22) Filed: Dec. 11, 2002

(65) Prior Publication Data

US 2003/0118508 A1 Jun. 26, 2003

Related U.S. Application Data

(60) Provisional application No. 60/340,665, filed on Dec. 13, 2001, provisional application No. 60/340,545, filed on Dec. 13, 2001.

(51) Int. Cl.
*A61K 51/00* (2006.01)
*A61M 36/14* (2006.01)

(52) U.S. Cl. .................... 424/9.1; 424/1.65; 424/1.11; 534/15

(58) Field of Classification Search ............... 424/1.11, 424/1.37, 1.65, 1.53, 1.49, 9.1, 9.3, 9.4, 9.5, 424/9.6, 9.7, 9.8; 534/7, 10–16; 514/1
See application file for complete search history.

(56) References Cited

U.S. PATENT DOCUMENTS

| | | | |
|---|---|---|---|
| 3,398,198 A | 8/1968 | Kersnar et al. | 260/584 |
| 3,726,912 A | 4/1973 | McCrary et al. | 260/513 N |
| 4,241,728 A * | 12/1980 | Mirell | 600/5 |
| 4,853,209 A | 8/1989 | Kaplan et al. | 424/1.1 |
| 4,882,142 A | 11/1989 | Simon et al. | 424/1.22 |
| 4,897,254 A | 1/1990 | Simon et al. | 424/1.1 |
| 4,898,724 A | 2/1990 | Simon et al. | 424/1.1 |
| 4,973,333 A | 11/1990 | Treharne | 606/77 |
| 4,976,950 A | 12/1990 | Simon et al. | 424/1.1 |
| 5,059,412 A | 10/1991 | Simon et al. | 424/1.1 |
| 5,064,633 A | 11/1991 | Simon et al. | 424/1.1 |
| 5,066,478 A | 11/1991 | Simon et al. | 424/1.1 |
| 5,300,279 A | 4/1994 | Simon et al. | 424/1.77 |
| 5,587,451 A | 12/1996 | Athey et al. | 528/345 |
| 5,707,610 A | 1/1998 | Ibsen et al. | 424/49 |
| 5,708,169 A | 1/1998 | Hester, Jr. et al. | 549/152 |
| 5,712,275 A | 1/1998 | Van Gestel | 514/222.5 |
| 5,714,467 A | 2/1998 | Boman et al. | 514/12 |
| 5,714,604 A | 2/1998 | Kiefer | 540/472 |
| 5,756,472 A | 5/1998 | Liesch et al. | 514/27 |
| 5,756,505 A | 5/1998 | Nishino et al. | 514/253 |
| 5,756,725 A | 5/1998 | Wilkening et al. | 540/302 |
| 5,760,063 A | 6/1998 | Lam et al. | 514/355 |
| 5,770,617 A | 6/1998 | La Voie et al. | 514/394 |
| 5,773,421 A | 6/1998 | Alder et al. | 514/25 |
| 5,773,443 A | 6/1998 | Ray et al. | 514/256 |
| 5,773,696 A | 6/1998 | Liang et al. | 800/205 |
| 5,783,570 A | 7/1998 | Yokota et al. | 514/56 |
| 5,786,325 A | 7/1998 | Borromeo et al. | 514/11 |
| 5,801,172 A | 9/1998 | Clapp-Shapiro et al. | 514/250 |
| 5,807,854 A | 9/1998 | Bartroli et al. | 514/248 |
| 5,814,634 A | 9/1998 | Nishino et al. | 514/237.8 |
| 5,824,698 A | 10/1998 | Häsler et al. | 514/394 |
| 5,824,874 A | 10/1998 | Ulbrich et al. | 800/205 |
| 5,830,855 A | 11/1998 | Takemoto | 514/11 |
| 5,830,889 A | 11/1998 | Iwata et al. | 514/195 |
| 5,837,253 A | 11/1998 | Cohen | 424/195.1 |
| 5,849,956 A | 12/1998 | Koga et al. | 568/326 |
| 5,854,213 A | 12/1998 | Bouffard | 514/11 |
| 5,854,280 A | 12/1998 | Gomez et al. | 514/456 |
| 5,856,347 A | 1/1999 | Hashiguchi et al. | 514/390 |
| 5,859,032 A | 1/1999 | Nishino et al. | 514/352 |
| 5,861,430 A | 1/1999 | Markonius | 514/456 |
| 5,863,773 A | 1/1999 | Gunawardana et al. | 435/118 |
| 5,866,549 A | 2/1999 | Or et al. | 514/29 |
| 5,872,249 A | 2/1999 | Park et al. | 540/225 |
| 5,873,726 A | 2/1999 | Gillbe | 434/29 |
| 5,876,738 A | 3/1999 | Ohno et al. | 424/404 |
| 5,888,526 A | 3/1999 | Tsubai et al. | 424/405 |
| 5,888,941 A | 3/1999 | Bartroli et al. | 504/262 |
| 5,891,890 A | 4/1999 | Nishino et al. | 514/331 |

(Continued)

FOREIGN PATENT DOCUMENTS

WO  WO 02/062398  8/2002

(Continued)

OTHER PUBLICATIONS

Oddzialu, et al., "An initial assessment of therapeutic value of strontium 85 isotope in treatment of chroni osteomyelitis in adults.", *Chir Narz Ruchu Ortop.*, vol. LVIII, No. 2, 1993, pp. 5454-5458, XP002235556, Poland. See Sumary.

(Continued)

*Primary Examiner*—Dameron L. Jones
(74) *Attorney, Agent, or Firm*—Elisabeth T. Jozwiak

(57) ABSTRACT

This invention relates to medical uses of radiopharmaceuticals. Specifically, the present invention relates to the use of radiopharmaceuticals to treat osteomyelitis. The present invention provides improved system and methods of for the direct delivery of radiopharmaceuticals to the site of osteomyelitis.

7 Claims, No Drawings

U.S. PATENT DOCUMENTS

| | | | |
|---|---|---|---|
| 5,908,862 A | 6/1999 | Wai Lee et al. | 514/546 |
| 5,910,498 A | 6/1999 | Yazaki et al. | 514/255 |
| 5,917,084 A | 6/1999 | Jiang | 560/174 |
| 5,919,438 A | 7/1999 | Saint-Leger | 424/70.1 |
| 5,919,925 A | 7/1999 | Burton et al. | 540/300 |
| 6,214,812 B1 | 4/2001 | Karpeisky et al. | 514/89 |
| 6,231,832 B1 | 5/2001 | Srivastava et al. | 424/1.65 |
| 6,491,893 B1* | 12/2002 | Babich | 424/1.11 |
| 2001/0041689 A1 | 11/2001 | Padioukova et al. | 514/79 |
| 2002/0176818 A1* | 11/2002 | Fritzberg et al. | 424/1.11 |
| 2002/0192157 A1* | 12/2002 | Low et al. | 424/1.49 |

FOREIGN PATENT DOCUMENTS

| | | |
|---|---|---|
| WO | WO 00/76556 | 12/2002 |

OTHER PUBLICATIONS

Bardiés, M. and Meyers, M. J., "Computational Methods in Radionuclide Dosimetry," *Phys. Med. Biol.* vol. 41, 1996, pp. 1941-1955.

Beddoe, A. H. et al., "Measurements of Trabecular Bone Structure in Man," *Phys. Med. Biol.* vol. 21, No. 4, 1976, pp. 589-607.

Bigler, R. E. and Woodard H. Q., "Skeletal Distribution of Mineralized Bone Tissue in Humans," *Health Physics* Pergamon Press vol. 31, Sep. 1976, pp. 213-218.

Champlin, R. and Gale, R. P., "Bone Marrow Transplantation for Acute Leukemia: Recent Advances and Comparison With Alternative Therapies," *Seminars in Hematology*, vol. 24, No. 1, Jan. 1987, pp. 55-67.

Champlin, R. and Gale, R. P., "Role of Bon Marrow Transplantation in the Treatment of Hematologic Malignancies and solid Tumors: Critical Review of Syngeneic, Autologous, and Allog neic Transplants," *Cancer Treatment Reports*, vol. 68, No. 1, Jan. 1984, pp. 145-161.

Eckerman, K. F. and Stabin M. G., "Dose Conversations In Factors for Marrow and Bone By Skeletal Regions," *The Journal of Nuclear Medicine*, vol. 35, No. 445, Wednesday, Jun. 8, 1994, pp. 112P.

Spiers, F. W. et al., "Mean Skeletal Dose Factors for Beta-Particle emitters in Human Bone. Part II: Surface-Seeking Radionuclides," *British Journal of Radiology*, vol. 54, 1981, pp. 500-504 (1981).

\* cited by examiner

TREATMENT OF OSTEOMYELITIS WITH RADIOPHARMACEUTICALS

This application claims the benefit of provisional application 60/340,665, filed Dec. 13, 2001, and provisional application 60/340,545, filed Dec. 31, 2001.

FIELD OF THE INVENTION

This invention relates to medical uses of radiopharmaceuticals. Specifically, the present invention relates to the use of radioisotope complexes to treat osteomyelitis.

BACKGROUND OF THE INVENTION

Osteomyelitis is infection in the bones. Often, the original site of infection is elsewhere in the body, and spreads to the bone by the blood. The bone may be predisposed to infection due to a recent minor trauma that results in a blood clot or hemostasis. In children, the long bones are usually affected. In adults, the vertebrae, head, and the pelvis are most commonly affected. Bacteria or fungi are the usual organisms, but any microbe may be responsible for the infection. Pus is produced within the bone, which may result in a bone abscess. The abscess then deprives the bone of blood supply. Chronic osteomyelitis results when the causative microbes become resistant to antimicrobial agents. This may occur due to development of cellular mechanisms to circumvent the antimicrobial agents, formation of biofilms which allow quiescent organisms to remain untouched by antimicrobial agents, death of bone tissue as a result of the lost blood supply, and other mechanisms. Chronic infection can persist for years with intermittent exacerbations. Risk factors for chronic infection are recent trauma, diabetes, hemodialysis patients, IV drug abuse, and infection with organisms that are more adept at forming biofilms or developing antimicrobial resistance. Tuberculous osteomyelitis is caused by tubercle bacilli that enter the bloodstream and settle in a bone. The disease progresses slowly and is chronic. Any bone may be infected but those most commonly involved are the vertebrae. Spinal tuberculosis, or "Pott's disease" causes bone destruction and spinal deformities. Other bones that may be affected are the longer bones of the hands or feet. The total incidence of osteomyelitis is 2 out of 10,000 people.

Symptoms of osteomyelitis primarily include pain in the bone, bone tenderness, local swelling and warmth (facial swelling), fever, nausea, general discomfort, uneasiness, or ill feeling (malaise), and drainage of pus through the skin in chronic infection. Additional symptoms include sweating, excessive chills, back pain, and low-grade swelling of the ankle, feet, or the leg. Osteomyelitis is diagnosed through physical examination showing bone tenderness, swelling and redness, elevated white blood cell count, elevated ESR, blood cultures that identify the causative organism, needle aspiration of vertebral space for culture, bone lesion biopsy and culture, bone scans, and drainage of a skin lesion with a sinus tract (the lesion "tunnels" under the tissues) for culture.

The outcome of treatment for acute osteomyelitis is usually good, but when treatment of acute osteomyelitis fails the outcome of treatment for chronic osteomyelitis is worse, even with surgery. Chronic infection may result in bone destruction, in stiffening of joints if the infection spreads to the joints, and, in extreme cases occurring before the end of the growth period, in the shortening of a limb if the growth center is destroyed. Resistant chronic osteomyelitis may result in amputation and can threaten life through seeding of the microorganisms to cardiac valves, the lungs, and the brain.

Treatment for osteomyelitis focuses on eliminating the infection and preventing the development of chronic infection. High-dose intravenous antibiotics are given initially. The type of antibiotics and the route of administration may later be changed depending on culture results. Typical lengths of treatment for acute osteomyelitis vary from 6 weeks to 6 months depending on the organism and the anatomy of the infection site. In chronic infection, surgical removal of dead bone tissue is indicated. The open space left by the removed bone tissue may be filled with bone graft or by packing material to promote the growth of new bone tissue. Antibiotic therapy is continued for at least 3 weeks after surgery. Infection of an orthopedic prosthesis requires surgical removal with debridement of the infected tissue surrounding the area. A new prosthesis may be implanted in the same operation, or delayed until the infection has resolved, depending on its severity. Estimates of the percentage of acute osteomyelitis cases that become chronic osteomyelitis cases vary from about 10% to about 30%. Once the osteomyelitis has become chronic, biofilms or abscesses usually have developed, protecting the microbes from treatment with antibiotic drugs.

The currently available antibiotic treatments are expensive, inconvenient, frequently ineffective, and subject to many complications. Thus, there is a need for additional therapies for osteomyelitis.

SUMMARY OF THE INVENTION

In one aspect, the present invention is a method for the treatment of osteomyelitis comprising: providing a subject suffering from osteomyelitis and a pharmaceutical composition comprising a radionuclide; and parenterally (usually intramuscularly or intravenously) administering the composition to the patient under conditions such that the osteomyelitis is reduced.

In a second aspect, the present invention is a method for the treatment of osteomyelitis comprising: locally administering a composition comprising a radionuclide to a subject suffering from osteomyelitis under conditions such that the osteomyelitis is reduced.

In a third aspect, the present invention is a method for the treatment of osteomyelitis comprising the steps of applying a tourniquet to a subject suffering from osteomyelitis; and administering a composition comprising a radionuclide to the subject under conditions such that the osteomyelitis is reduced. The present invention provides improved system and methods of for the direct delivery of radiopharmaceuticals to the site of osteomyelitis.

The present invention provides improved system and methods of for the direct delivery of radiopharmaceuticals to the site of osteomyelitis.

DESCRIPTION OF THE INVENTION

Before the present compositions and methods are described, it should be noted that the present invention is not limited to the particular methodology and compositions described herein as these may vary. It should also be understood that the terminology used herein is for the purpose of describing particular aspects of the invention, and is not intended to limit its scope, which will be limited only by the appended claims.

It must be noted that as used herein and in the appended claims, the singular forms "a", "an", and "the" include plural reference unless the context clearly dictates otherwise. Thus, for example, reference to "a subject" includes a plurality of such subjects, reference to the "radionuclide" is a reference to one or more radionuclides and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the compositions and methodologies that are reported in the publications which might be used in connection with the invention. Nothing herein is to be construed as an admission that the invention is not entitled to antedate such disclosure by virtue of prior invention.

As used herein, the term "disease" refers to pathologies and deleterious conditions, such as infections, inflammatory responses, cancer, autoimmune, and genetic disorders.

As used herein the term "microorganism" refers to microscopic organisms and taxonomically related macroscopic organisms within the categories of algae, bacteria, fungi (including lichens), protozoa, viruses, and subviral agents. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen" refers to an organism (including microorganisms) that causes disease in another organism (e.g., animals and plants) by directly infecting the other organism, or by producing agents that cause disease in another organism (e.g., bacteria that produce pathogenic toxins and the like).

As used herein, the term "osteomyelitis" refers to an infection of the bone. Osteomyelitis infections are generally caused by a pathogenic microorganism (e.g., a bacteria or a fungus). Osteomyelitis includes both acute and chronic (e.g., persistent) bone infections.

"Systemic infection" as used herein denotes infection throughout a substantial part of an organism including mechanisms of spread other than mere direct cell inoculation but rather including transport from one infected cell to additional cells either nearby or distant.

As used herein, term "subject suffering from osteomyelitis" refers to a subject that has one or more symptoms of osteomyelitis (e.g., including but not limited to, pain in the bone, bone tenderness, and swelling or warmth) or a positive diagnosis based on one or more diagnostic tests (e.g., including but not limited to, a bone scan, blood culture, or culture of the infectious lesion).

As used herein, the term "subject suffering from osteomyelitis at a particular site of infection" refers to a "subject suffering from osteomyelitis" wherein the osteomyelitis has been identified as being in a particular bone or region of bone or in several particular bones or regions of bones.

As used herein, the term "such that said osteomyelitis is reduced" refers to the reduction of infection based on the lack of one or more symptoms of osteomyelitis (e.g., including but not limited to, pain in the bone, bone tenderness, and swelling or warmth) or a negative diagnosis based on one or more diagnostic tests (e.g., including but not limited to, a bone scan, blood culture, or culture of the infectious lesion).

As used herein, the term "radionuclide" refers to a nuclide that disintegrates with the emission of corpuscular or electromagnetic radiation. As used herein, the term "nuclide" refers to a species of atom characterized by the charge, mass number and quantum state of its nucleus that is stable for a measurable lifetime (e.g., greater than $10^{-10}$ seconds). The methods of the present invention are not limited to a particular radionuclide. Any suitable radionuclide may be utilized, including but not limited to, those disclosed herein.

As used herein, the term "pharmaceutical composition comprising a radionuclide" refers to any pharmaceutically acceptable composition that comprises a radionuclide and any sterile, biocompatible pharmaceutical carrier. Pharmaceutical compounds may also include additional active agents such as, including but not limited to, ligands complexed to the radionuclides.

The terms "pharmaceutically acceptable" and "pharmacologically acceptable," as used herein, refer to compositions that do not substantially produce adverse allergic, immunological or other reactions when administered to a host (e.g., an animal such as a human). As used herein, "pharmaceutically acceptable carrier" includes any and all solvents (e.g., including but not limited to, saline, buffered saline, dextrose and water), dispersion media, coatings, wetting agents (e.g., sodium lauryl sulfate), isotonic and absorption delaying agents, disintrigrants (e.g., potato starch or sodium starch glycolate), and the like.

As used herein, the term "locally administering a composition comprising a radionuclide to subject suffering from osteomyelitis at said site of infection" refers to administering a pharmaceutical composition of the present invention directly to the site of osteomyelitis (e.g., a limb bone).

As used herein, the term "ligand" refers to any compound capable of physically interacting with a radionuclide of the present invention. In some embodiments, the radionuclide is chelated by electron donor groups of the ligand. However, any interaction that results in stable complexes when administered to a subject using the methods of the present invention is suitable. The term "ligand" is also not intended to be limited by the chemical nature of the compound. In preferred embodiments, a macrocyclic or acyclic aminophosphonic acid is used as a ligand for complexing with a radionuclide of the present invention.

The term "cyclic compounds" refers to compounds having one (i.e., a monocyclic compounds) or more than one (i.e., polycyclic compounds) ring of atoms. The term is not limited to compounds with rings containing a particular number of atoms. While most cyclic compounds contain rings with five or six atoms, rings with other numbers of atoms (e.g., three, four, or twelve atoms) are also contemplated by the present invention. The identity of the atoms in the rings is not limited, though the atoms are usually predominantly carbon atoms. Generally speaking, the rings of polycyclic compounds are adjacent to one another. However, the term "polycyclic compound" includes those compounds containing multiple rings that are not adjacent to each other.

The terms "macrocyclic compound" and "macrocycle" refer to a "cyclic compound" with a ring containing more than about eight atoms.

The term "heterocyclic compounds" refers broadly to cyclic compounds wherein one or more of the rings contains more than one type of atom. In general, carbon represents the predominant atom, while the other atoms include, for example, nitrogen, sulfur, and oxygen. Examples of heterocyclic compounds include benzimidazole, furan, pyrrole, thiophene, and pyridine.

As used herein, the term "parenteral administration" includes all routes of administering an agent (e.g., a pharmaceutical composition of the present invention) that are not through the gastrointestinal route. Examples of parenteral administration include, but are not limited to, intravenous, intra-arterial, intramuscular, local, subcutaneous, intradermal, and transcutaneous administration.

The terms "aromatic," "aromatic compounds," and the like refer broadly to compounds with rings of atoms having delocalized electrons. The monocyclic compound benzene ($C_6H_6$) is a common aromatic compound. However, electron delocalization can occur over more than one adjacent ring (e.g., naphthalene [two rings] and anthracene [three rings]). Different classes of aromatic compounds include, but are not limited to, aromatic halides (aryl halides), aromatic heterocyclic compounds, aromatic hydrocarbons (arenes), and aromatic nitro compounds (aryl nitro compounds).

As used herein the terms "meta substitution" and "meta position" when used in terms of substituted benzenes, refer to benzene derivatives substituted at positions 1 and 3 or 1 and 5 (i.e., each of the 6 carbons of the 6 membered benzene ring is numbered consecutively). As used herein, the terms "para substitution" and "para position" when used in terms of substituted benzenes, refer to benzene derivatives substituted at positions 1 and 4 of the benzene ring.

As used herein, the terms "aliphatic" and "aliphatic compounds" refer to compounds which comprise carbon atoms in chains, rather than the ring structure of cyclic compounds.

The term "mixture" refers to a mingling together of two or more substances without the occurrence of a reaction by which they would lose their individual properties. The term "solution" refers to a liquid mixture. The term "aqueous solution" refers to a solution that contains some water. In many instances, water serves as the diluent for solid substances to create a solution containing those substances. In other instances, solid substances are merely carried in the aqueous solution (i.e., they are not dissolved therein and are a "mixture" of an aqueous solution and the non-dissolved solid substances). The term aqueous solution also refers to the combination of one or more other liquid substances with water to form a multi-component solution.

"Acylate" as used herein, refers to the introduction of an acyl group into a molecule, (i.e., acylation).

"Biologically active", as used herein, refers to a molecule having the structural, regulatory, or biochemical functions of a naturally occurring molecule.

"Cell culture" as used herein, refers to a proliferating mass of cells that may be in either an undifferentiated or differentiated state.

"Immunologically active" refers to the capability of a natural, recombinant, or synthetic polypeptide, or any oligopeptide thereof, to bind with specific antibodies and induce a specific immune response in appropriate animals or cells.

"Purified" as used herein when referring to a chemical compound or molecule, indicates that the molecule is present in the substantial absence of other chemical or biological compounds of the same type. The term "purified" as used herein preferably means at least 95% by weight, more preferably at least 99.8% by weight, of molecules of the same type present.

The term "pure" as used herein preferably has the same numerical limits as "purified" immediately above.

"Sample" as used herein, is used in its broadest sense. A biological sample may comprise a tissue, a cell, an extract from cells, blood, serum, and other bodily fluids.

The present invention provides methods for the treatment of osteomyelitis. Osteomyelitis is often diagnosed by a nuclear medicine bone scan using known radiopharmaceutical agents. The radiopharmaceuticals concentrate at the site of bone infection to show the presence of infection. Radiopharmaceuticals have also been used to treat bone cancers, arthritis, and to ablate bone marrow.

Accordingly, the present invention provides methods for the use of radiopharmaceuticals to treat osteomyelitis. The methods of the present invention find use in the treatment of all forms of osteomyelitis (e.g., acute or chronic infection). The present invention further provides delivery methods that increase the localization of the radioactivity to the bone, thus reducing the systemic radiation dose.

The methods and compositions described below are exemplary and are not intended to limit the scope of the invention. One skilled in the relevant art recognizes that additional suitable radiopharmaceuticals, ligands, dosages, and treatment formulations may be substituted for those disclosed herein.

I. Radiopharmaceuticals

The present invention provides radiopharmaceuticals for the treatment of osteomyelitis. The invention is not limited to a particular radioisotope or ligand. Any suitable radioisotope or ligand that functions to treat osteomyelitis may be utilized, including but not limited to, those disclosed herein. Guidance for selecting and screening agents for use in the methods of the present invention are described below.

A. Radionuclides

The radiopharmaceutical compositions of the present invention comprise one or more radionuclides. In preferred embodiments, the half-life of the radionuclides is sufficiently long to allow for localization and delivery of the complex in the bone tissue while still retaining sufficient radioactivity to kill pathogens present in the bone. Generally, it is preferred to use a radionuclide-ligand complex that results in rapid biolocalization of the radionuclide in the bone tissue so as to achieve rapid onset of pathogen irradiation. In preferred embodiments, a radionuclide having sufficient alpha or beta energy is utilized.

By preferentially delivering the radionuclide to the site of active bone infection, the radiation can be performed with nuclides that emit radiation with relatively short path lengths before absorption (e.g., beta radiation) with good microbe kill and less damage to other tissues. In addition, directly targeting the radionuclide to the site of infections allows the use of a nuclide with a relatively short half life (e.g., one or two days) that delivers its radiation dose quickly. This results in a higher likelihood that more of the pathogen will be killed. This is in direct contrast to the currently available methods of delivering a lower per minute dose of radiation over a longer time period that has the potential to allow more bacteria to repair any radiation damage and survive the treatment.

For example, in some embodiments, radionuclides utilized in the methods of the present invention exhibit beta energy >0.5 MeV, preferably >1 MeV with an effective half-life of about <5 days, preferably <3 days. Radionuclides useful in the methods and compositions of the present invention include, but are not limited to, Arsenic-77 ($^{77}$As), Molybdenum-99 ($^{99}$Mo), Rhodium-105 ($^{105}$Rh), Lutetium-177 ($^{177}$Lu), Cadmium-115 (115Cd), Antimony-122 ($^{122}$Sb), Promethium-149 (149Pr), Osmium-193 ($^{193}$Os), Gold-198

($^{198}$Au), Tin-117m ($^{177m}$Sn), Strontium-89 ($^{89}$Sr), Thorium-200 ($^{200}$Th) Indium-115 ($^{115}$In), Dysprosium-165 ($^{165}$Dy), Lanthanum-140 ($^{140}$La), Ytterbium-175 ($^{175}$Yb), Scandium-47 ($^{47}$Sc); preferably Samarium-153 ($^{153}$Sm), Yttrium-90 ($^{90}$Y), Gadolinium-159 ($^{159}$Gd), Rhenium-186 ($^{186}$Re), Rhenium-188 ($^{188}$Re), and Holmium-166 ($^{166}$Ho). Especially preferred is $^{166}$Ho, which emits high-energy beta particles and gamma radiation (80 KeV, 6.0%) useful for imaging and exhibits a half-life of 26.8 hr. In other embodiments, alpha emitters such as Actinium-225 ($^{225}$Ac), Bismuth-212 ($^{212}$Bi) and Bismuth-213 ($^{213}$Bi) are utilized.

The respective radionuclides can be obtained using procedures well known in the art. Typically, the desired radionuclide can be prepared by bombarding an appropriate target, such as a metal, metal oxide, or salt with neutrons. Another method of obtaining radionuclides is by bombarding nuclides with particles in a linear accelerator or cyclotron. Yet another way of obtaining radionuclides is to isolate them from fission product mixtures. The present invention is not limited to a particular method of obtaining radionuclides. Any suitable method that results in the generation of the desired radionuclide may be utilized.

B. Ligands

In some embodiments of the present invention, radionuclides are conjugated to pharmaceutically acceptable ligands. In particularly preferred embodiments, aminophosphonic acids, particularly macrocyclic and acyclic aminophosphonic acids, are utilized as ligands. These compounds are prepared by any suitable technique. Known synthetic techniques involve reacting a compound containing at least one reactive amine hydrogen with a carbonyl compound (aldehyde or ketone) and a phosphorous acid or appropriate derivative thereof.

Methods for carboxyalkylating macrocyclic amines to give amine derivatives containing a carboxyalkyl group are disclosed in U.S. Pat. No. 3,726,912, herein incorporated by reference. Methods to prepare alkylphosphonic acid amines and hydroxyalkylamines are disclosed in U.S. Pat. Nos. 3,398,198, 5,066,478, and 5,300,279, each of which is herein incorporated by reference.

The amine precursor (1,4,7,10-tetraazacyclododecane) employed in making certain of the macrocyclic aminophosphonic acids utilized in some embodiments of the present invention is a commercially available material. The preparation of macrocyclic aminophosphonic ligands can also be found in U.S. Pat. No. 5,059,412, herein incorporated by reference. The preparation of these ligands has also been described in U.S. Pat. Nos. 4,973,333, 4,882,142, 4,853,209, 4,898,724, 4,897,254, 5,587,451, 5,714,604, 5,064,633, 5,587,451, 5,066,478, 5,300,279, 5,059,412, and 5,064,633, each of which is herein incorporated by reference. In preferred embodiments, ligands are selected from the group consisting of ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), 1,4,7,10-tetraazacyclododecanetetramethylenephosphonic acid (DOTMP), tris(2-aminoethyl)amine hexamethylene-phosphonic acid (TTHMP), methylene diphosphonate, hydroxymethylenediphosphonate, hydroxyethylidene diphosphonate (HEDP), and ethane-1-hydroxy-1,1-diphosphonic acid. In particularly preferred embodiments, ligands are macrocyclic aminophosphonic acid ligands of which 1,4,7,10-tetraazacyclododecanetetramethylenephosphonic acid (DOTMP) is an example.

In addition to phosphorus based chelates, aminocarboxylic acids such as diethylenetriaminepentaacetic acid can also be used to deliver isotopes to bone tissue. For example, U.S. Pat. No. 6,231,832 teaches the delivery of Sn-117m to bone using such a chelator. Also, U.S. Pat. No. 4,897,254 teaches the uses of hydroxyethylethylenediaminetriacetic acid in combination with Sm-153 to deliver a radiation dose to bone.

C. Radionuclide-Ligand Complexes

In preferred embodiments, the methods and compositions of the present invention employ complexes of radionuclides and ligands. The complexes may be generated using any suitable method, including but not limited to, those disclosed herein. In preferred embodiments, the radionuclide complex must be taken up preferentially by bone so that it is possible to deliver radiation to the bone with minimal exposure to other tissues such as lung, liver, bladder or kidneys. In is also preferred that the radionuclide complex be rapidly cleared from the blood, thereby further reducing exposure to non-target tissues.

The radionuclide and ligand are combined under any conditions that allow the two to form a complex. Generally, mixing in water at a controlled pH (the choice of pH is dependent upon the choice of ligand and radionuclide) is suitable. The complex is formed by chelation of the radionuclide by an electron donor group or groups that results in a stable radionuclide complex (e.g., stable to the disassociation of the radionuclide from the ligand). For example, $^{166}$Ho-DOTMP is formed by adding a $^{166}$Ho salt, such as the chloride or nitrate in aqueous HCl (0.1–1 N), to a sterile, evacuated vial containing at least 3 equivalents of DOTMP in aqueous base (KOH, NaOH and the like). After stirring at a pH of 10.5, the pH is then adjusted to 7–8 by adding phosphate buffer and a stabilizing agent such as ascorbic acid. Complexation of >99% is generally achieved using such a method.

For the purpose of the present invention, radionuclide compositions described herein and physiologically acceptable salts thereof are considered equivalent. Physiologically acceptable salts refer to the acid addition salts of those bases which will form a salt with at least one acid group of the ligand or ligands employed and which will not cause adverse physiological effects when administered as described herein. Suitable bases include, but are not limited to, for example, the alkali metal and alkaline earth metal hydroxides, carbonates, and bicarbonates such as, for example, sodium hydroxide, potassium hydroxide, calcium hydroxide, potassium carbonate, sodium bicarbonate, magnesium carbonate and the like, amine hydroxides, carbonates, and bicarbonates such as, for example, ammonium hyroxide, ammonium carbonate, and the like, or primary secondary and tertiary amine hydroxides, carbonates, and bicarbonates such as, for example, trimethyl ammonium carbonate and the like. Physiologically acceptable salts can be prepared by treating the macrocyclic aminophosphonic acid with an appropriate base.

The macrocyclic aminophosphonic acid complexes when formed at approximately a ligand to metal molar ratio of 1:1 to 20:1 give biodistributions that are consistent with those exhibited by known agents that are bone-specific. The optimum ratio depends on the particular ligand utilized. Preferred osteomyelitic treating radionuclide compositions include $^{166}$Ho-DOTMP, $^{177}$Lu-DOTMP, and $^{153}$Sm-EDTMP. Preferably, molar ratios of DOTMP to $^{166}$Ho are above 1, e.g., from 1.5 to 3.5:1. The most preferred ratio is about 3.5:1. Such a ratio provides adequate complexation of the radionuclide while compensating for radiolysis of the ligand. By contrast, other acyclic aminophosphonic acid complexes can result in substantial localization of radioactivity in soft tissue (e.g., liver) if large excess amounts of ligand are not used. Large excesses of ligand are undesirable since uncomplexed ligand may be toxic to the patient or may result in cardiac arrest or hypocalcemic convulsions. In addition, the macrocyclic aminophosphonic acid ligands are useful when large amounts of metal are required (i.e. for metals that have a low specific activity). In this case, the macrocyclic aminophosphonic acid ligands have the ability to deposit more tolerable doses of radioactivity in the bone than is possible when using non-cyclic aminophosphonic acid ligands.

In the case of other ligands, such as EDTMP, a large excess of ligand is necessary. The most preferred ratio of EDTMP to Sm is 273:1. Aminocarboxylic acid ligands are also preferably present in large excess over radionuclide.

D. Pharmaceutical Compositions

In preferred embodiments, radionuclides and radionuclide-ligand complexes are administered as pharmaceutically acceptable compositions. A pharmaceutically acceptable means of protecting the radionuclide complex from radiolytic decay of the chelator is highly preferred. Preferred radioprotectants of the present invention are radio-stable anti-oxidants, compounds that either reduce the number or the activity of oxidizing radicals. Exemplary radio protectants that can be employed in the practice of the present invention are ascorbic acid, gentisic acid, nicotinic acid, ascorbyl palmitate, HOP(:O) $H_2$, monothioglycerol, sodium formaldehyde sulfoxylate, $Na_2S_2O_3$, $SO_2$, or a reducing agent combined with BHA, BHT, pyrogallate, tocopherol, and the like. Ascorbic acid is the preferred radioprotectant for use in the practice of the present invention, and can be used at about 35–75 mg/ml of liquid composition. This concentration of ascorbate can provide a solution of $^{166}$Ho-DOTMP that is stable (e.g., therapeutically useful), for at least 72 hours at ambient conditions (e.g., unfrozen).

The formulations of the present invention are in the solid or preferably liquid form containing the active radionuclide complexed with the ligand. These formulations can be in kit form such that the chelator and radionuclide are mixed at the appropriate time prior to use in a suitable liquid carrier with the radioprotectant. Whether premixed or as a kit, the formulations usually require a pharmaceutically acceptable carrier, such as water.

The pharmaceutical dosage forms suitable for injection or infusion can include sterile solutions, dispersions, emulsions, or microemulsions, comprising the active ingredients that are adapted for the extemporaneous preparation of sterile injectable or infusible solutions or dispersions, optionally encapsulated in protective matrices such as nanoparticles or microparticles. In all cases, the ultimate dosage form must be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), DMSO, and suitable mixtures thereof. In many cases, it will be preferable to include isotonic agents, for example, sugars, buffers or sodium chloride.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethyl cellulose solutions. If necessary to keep the complex in suspension, suitable physiologically acceptable adjuvants can be chosen from among thickeners such as, for example, carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylenesorbitan esters. Many substances that effect the hydrophobicity, density, and surface tension of the liquid suspension medium can assist in making injectable suspensions in individual cases. For example, silicone antifoams, sorbitol, and sugars are all useful suspending agents.

II. Treatment of Osteomyelitis

The present invention provides novel methods of treating osteomyelitis using radiopharmaceutical compositions. In some preferred embodiments, the compositions are delivered directly to the site of infection, thus decreasing the amount of radioactivity required to reduce infection. The present invention is not limited to the dosages and methods of administration described below. One skilled in the art recognizes that other suitable dosages and administration methods may be utilized in the practice of the present invention.

A. Dosages

The effective therapeutic amount of radionuclide composition administered to achieve elimination of osteomyelitis will vary according to factors such as the age, weight and health of the patient, the disease state being treated (e.g., chronic or acute infection), the treatment regimen selected (e.g., mode of administration), the amount of oxygen in the system, as well as the nature of the particular radionuclide composition to be administered. For example, less activity will be needed for radionuclides with longer half lives. The energy of the emissions will also be a factor in determining the amount of activity necessary. In some embodiments, a dose of about 10 to 1000 Gy is used. Preferably, a total dose of about 20–60 Gy, most preferably about 30–60 Gy, e.g., 40–50 Gy of radiation is delivered to bone parenterally (e.g., preferably via intramuscular injection or locally).

The radiation exposure is reported using the Grey scale (Gy). One Gy is equivalent to 100 Rads. A rad is defined as adsorbed energy of 100 ergs per gram. Because the biodistribution of radiopharmaceuticals vary from patient to patient, it is preferred to first administer a small dose and determine the biodistribution of the agent prior to giving the therapeutic dose. Radioactivity measurements of the isotope in blood, urine, bone, and infected areas are used to estimate the dose to the target and non-target areas. This is translated into a therapeutic dose for the individual patient. For example, in some embodiments, a diagnostic dose of about 1110–1850 MBq (about 30 mCi to about 50 mCi) of Ho-166-DOTMP is used as a diagnostic dose to determine the therapeutic dose. Alternatively, a different agent, such as Tc-99m-MDP, that has a very similar biodistribution as the therapeutic agent can be given prior to the therapeutic dose. Determination of the doses of radiation delivered by the present complexes can be determined in accord with known methodologies (See e.g., Bardies et al., Physics in Medicine and Biology, 41,1941 (1996); Beddoe et al., Physics in Medicine & Biology, 21, 589 (1976); Bigler et al., Health Physics, 31, 213 (1976); Champlin et al., Semin. Hematol, 24, 55 (1987); Champlin et al., Cancer Treatment Reports, 68, 145 (1984); Eckerman et al., Journal of Nuclear Medicine, 35, 112P (1994); Spiers et al., British Journal of Radiology, 54, 500 (1981)).

B. Additional Therapeutic Agents

In some embodiments, radiopharmaceuticals are administered in combination with additional agents (e.g., including but not limited to, antibacterial, anti-parasitic, and antifungal agents, including those disclosed in The Physicians Desk Reference, 50th Edition, 1996).

Useful antibiotic agents include systemic antibiotics, such as aminoglycosides, cephalosporins (e.g., first, second, and third generation), macrolides (e.g., erythromycins), monobactams, penicillins, quinolones, sulfonamides, and tetracyclines, including those disclosed in The Physicians Desk Reference, 50th Edition, 1996. In addition, antibacterial agents include 2-isocephem and oxacephem derivatives disclosed in U.S. Pat. No. 5,919,925, herein incorporated by reference; pyridone carboxylic acid derivatives disclosed in U.S. Pat. No. 5,910,498, herein incorporated by reference; water miscible esters of mono- and diglycerides disclosed in U.S. Pat. No. 5,908,862, herein incorporated by reference; benzamide derivatives disclosed in U.S. Pat. No. 5,891,890, herein incorporated by reference; 3-ammoniopropenyl cephalosporin compounds disclosed in U.S. Pat. No. 5,872,249; 6-O-substituted ketolides disclosed in U.S. Pat. No. 5,866,549, herein incorporated by reference; benzopyran phenol derivatives disclosed in U.S. Pat. No. 5,861,430, herein incorporated by reference; pyridine derivatives disclosed in U.S. Pat. No. 5,859,032, herein incorporated by reference; 2-aminothiazole derivatives disclosed in U.S. Pat. No. 5,856,347, herein incorporated by reference; penem ester derivatives disclosed in U.S. Pat. No. 5,830,889, herein incorporated by reference; lipodepsipeptides disclosed in U.S. Pat. No. 5,830,855, herein incorporated by reference; dibenzimidazole derivatives disclosed in U.S. Pat. No. 5,824,698, herein incorporated by reference; alkylenediamine derivatives disclosed in U.S. Pat. No. 5,814,634, herein incorporated by reference; organic solvent-soluble mucopolysaccharides disclosed in U.S. Pat. No. 5,783,570, herein incorporated by reference; arylhydrazone derivatives disclosed in U.S. Pat. No. 5,760,063, herein incorporated by reference; carbapenem compounds disclosed in U.S. Pat. No. 5,756,725, herein incorporated by reference; N-acylpiperazine derivatives disclosed in U.S. Pat. No. 5,756,505, herein incorporated by reference; peptides disclosed in U.S. Pat. No. 5,714,467, herein incorporated by reference; oxathiazines and their oxides disclosed in U.S. Pat. No. 5,712,275, herein incorporated by reference; 5-amidomethyl alpha beta-saturated and -unsaturated 3-aryl butyolactone compounds disclosed in U.S. Pat. No. 5,708,169, herein incorporated by reference; halogenated benzene derivatives disclosed in U.S. Pat. No. 5,919,438, herein incorporated by reference; sulfur-containing heterocyclic compounds disclosed in U.S. Pat. No. 5,888,526, herein incorporated by reference; and oral antibacterial agents disclosed in U.S. Pat. No. 5,707,610, herein incorporated by reference.

Antifungal agents include dermatological fungicides, topical fungicides, systemic fungicides, and vaginal fungicides, including those disclosed in The Physicians Desk Reference, 50th Edition, 1996. In addition, antifungal agents include terpenes, sesquiterpenes, diterpenes, and triterpenes disclosed in U.S. Pat. No. 5,917,084, herein incorporated by reference; sulfur-containing heterocyclic compounds disclosed in U.S. Pat. No. 5,888,526, herein incorporated by reference; carbozarnides disclosed in U.S. Pat. No. 5,888,941, herein incorporated by reference; phyllosilicates disclosed in U.S. Pat. No. 5,876,738, herein incorporated by reference; corynrcandin derivatives disclosed in U.S. Pat. No. 5,863,773, herein incorporated by reference; sordaridin derivatives disclosed in U.S. Pat. No. 5,854,280, herein incorporated by reference; cyclohexapeptides disclosed in U.S. Pat. No. 5,854,213, herein incorporated by reference; terpene compounds disclosed in U.S. Pat. No. 5,849,956, herein incorporated by reference; agents derived from aspergillus furnigatus disclosed in U.S. Pat. No. 5,873,726, herein incorporated by reference; inula extracts disclosed in U.S. Pat. No. 5,837,253, herein incorporated by reference; lipodepsipeptides disclosed in U.S. Pat. No. 5,830,855, herein incorporated by reference; polypeptides disclosed in U.S. Pat. No. 5,824,874, herein incorporated by reference; pyrimidone derivatives disclosed in U.S. Pat. No. 5,807,854, herein incorporated by reference; agents from spororniella minimizes disclosed in U.S. Pat. No. 5,801,172, herein incorporated by reference; cyclic peptides disclosed in U.S. Pat. No. 5,786,325, herein incorporated by reference; polypeptides disclosed in U.S. Pat. No. 5,773,696, herein incorporated by reference; triazoles disclosed in U.S. Pat. No. 5,773,443, herein incorporated by reference; fusacandins disclosed in U.S. Pat. No. 5,773,421, herein incorporated by reference; terbenzimidazoles disclosed in U.S. Pat. No. 5,770,617, herein incorporated by reference; and agents obtained from hormones disclosed in U.S. Pat. No. 5,756,472, herein incorporated by reference.

C. Delivery of Radiopharmaceuticals

The present invention contemplates the use of radiopharmaceuticals to treat osteomyelitis in animals, including but not limited to, humans. The methods of the present invention are suitable to treat acute or chronic osteomyelitis in any bone. Suitable radiopharmaceuticals, ligands, and dosages include, but are not limited to, those described above. One skilled in the relevant art understands how to determine suitable compositions and dosages for a specific animal and site or extent of infection.

The direct administration methods of the present invention provide the advantage of delivering an increased concentration of the radionuclide to the affected area and decreasing the exposure of the rest of the body. This is in contrast to systemic intravenous injection of bone agents, which results in radioactivity deposited in the entire skeletal system of the subject. The dose from the bone to the bone marrow is of most concern. This is especially true of radionuclides such as Ho-166 or Y-90 that are high-energy beta emitters. If a portion of the marrow can be spared from radioactivity, then it is probable that the affected area will regenerate without putting the patient at risk. Application to the infected area after isolating the blood flow using an arterial obstruction device, such as a tourniquet, will result in a larger dose to the infected area and reduce the dose to bone marrow. Similarly, application of one or more arterial obstruction devices to isolate portions of the skeletal system from the site of injection of the radionuclide will protect those portions of the bone marrow.

Accordingly, in preferred embodiments, radiopharmaceuticals are administered locally to the area of the infected bone. Local administration can be performed by techniques known in the art, including but are not limited to, intravenous injection, intra-arterial injection, intramuscular injection, subcutaneous injection, intraosseous injection, and transcutaneous administration. In some embodiments, radiopharmaceuticals are injected intramuscularly near the site of infection.

In some preferred embodiments, a tourniquet or other arterial obstruction device is placed above the area of injection in order to aid in the localization of the radiopharmaceuticals. In some embodiments, the tourniquet is placed on the limb prior to injection and removed immediately following injection. In preferred embodiments, the tourniquet is left in place for a short period of time following injection (e.g., long enough for the radiopharmaceutical to localize to the site of infection). In preferred embodiments, the tourniquet is left in place for greater than 2 minutes (e.g., preferably 5 minutes and more preferably 10 minutes) and then removed. It is preferred that the tourniquet is left in place no greater than 60 minutes in order to avoid hypoxic damage to the tissues due to restricted blood flow.

In other embodiments (e.g., where the osteomyelitis is located in an area proximal to the most proximal limb location for a tourniquet, such as in a rib, vertebrae, pelvis, femoral head, humeral head, clavicle, scapula, skull, or mandible), tourniquets are applied to one or more extremities to prevent access of the radiopharmaceutical agent to these areas. For instance, in some embodiments, tourniquets are applied proximally to each leg to protect the bone marrow in the legs from exposure to the radiopharmaceutical. The radiopharmaceutical agent is then given intravenously into a brachial vein to be carried through the blood stream to an osteomyelitis site, for instance in the mandible or the vertebral column. The tourniquet is then removed after an appropriate time (less than 60 minutes but greater than 2 minutes, more preferably greater than 5 minutes, most preferably about 10 minutes) after injection.

In some embodiments, radiopharmaceuticals are administered with additional antibacterial or fungal agents. Suitable agents include, but are not limited to, those described above.

In preferred embodiments, administration of a radiopharmaceutical agent result in the reduction of osteomyelitis (e.g., as determined by a bone scan). If the infection is not sufficiently reduced or eliminated, additional doses of radiopharmaceuticals are given. Alternatively, or in combination, increased doses of radiopharmaceuticals are administered until symptoms and diagnostic tests reveal that the infection is eliminated.

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); U (units), mU (milliunits); Ci (Curie); min. (minutes); sec. (seconds); and % (percent).

Example 1

Preparation of $^{166}$Ho-DOTMP

165-Ho-nitrate targets are prepared from dissolution of holmium oxide in nitric acid followed by reduction to dryness. A target containing 6 mg of holmium is irradiated in a reactor for approximately 155 hours at a flux of $4.5 \times 10^{14}$ n/cm$^2$/s. The specific activity is typically in the range of 1.3–2 Ci/mg.

The 66Ho-nitrate target is dissolved in 0.3 N HCl. In a typical 9 Ci preparation, $^{166}$Ho-chloride is supplied from the reactor in 10 ml of 0.3 N HCl. DOTMP (60 mg DOTMP and 168 mg NaOH) is dissolved in 4 ml water and added to the $^{166}$Ho chloride. The ligand to metal ratio is 3.5. The reaction mixture is allowed to mix for 10 minutes at a pH of 10.5. This is followed by addition of 4.8 ml of 1.0 M sodium phosphate buffer and ascorbic acid. The final concentration of ascorbic acid is 55 mg/ml. Dilution with water is performed to assure that the final activity concentration does not exceed 322 mCi/ml. The pH of the final product is 7–8.

Example 2

Treatment of Osteomyelitis in Rats with $^{166}$Ho-DOTMP

This example describes the successful treatment of osteomyelitis in rats using $^{166}$Ho-DOTMP. Four 150 g male Sprague Dawley rats were anesthetized and prepared for surgery by shaving the left leg. The skin over the left tibia and fibula was opened, a hole was drilled into the bone marrow, and an 18-gauge needle was inserted into the bone marrow. Through the needle, a piece of 0 surgical suture and approximately 0.1 ml of *Staphylococcus aureus* culture in Trypticase soy broth were introduced into the bone marrow. The needle was removed and the bone defect sealed with cyanoacrylate glue. The skin was closed with 0 surgical suture. The rats were followed with serial radiographs of the left leg. Lytic lesions diagnostic of osteomyelitis developed in the fibula over the next three weeks. The entire bone appeared radiolucent.

Two rats were followed without treatment. One week later, both of the rats died. Necropsy revealed that the tibia was eroded with only a very thin layer of bone encasing a thick fluid. Culture of the fluid grew Gram positive cocci consistent with the original *Staphylococcus aureus* infection.

Two rats were treated with $^{166}$Ho-DOTMP. A tourniquet was placed on the left leg above the knee. An intramuscular injection of 30 Gray (9 milliCurie) of $^{166}$Ho-DOTMP was given after application of the tourniquet. The tourniquet was released after 10 minutes. The rats were followed with continued serial radiographs of the leg. The radiographs showed a return to normal appearance of the tibia and fibula in two weeks.

Examples 3 Through 6

Biodistribution of radiopharmaceuticals in rats with and without the application of a tourniquet to a limb bone.

A. Methods

1. Preparation of DOTMP and EDTMP

DOTMP and EDTMP were prepared according to methods described in U.S. Pat. Nos. 4,898,724 and 4,976,950.

2. Preparation of Holmium and Samarium radionuclide solutions Ho-166, obtained from the University of Missouri Research Reactor, Columbia Mo., was dissolved in 0.1N HCl to yield a $6 \times 10^{-3}$ M $^{166}$HoCl$_3$ solution. Sm-153, obtained from the University of Missouri Research Reactor, Columbia, Mo., was dissolved in 0.1 N HCl to yield a $6.6 \times 10^{-3}$ M solution.

The radioactive $^{166}$HoCl3 solution was then mixed with non-radioactive $^{165}$HoCl3 solutions to prepare solutions that would have only a tracer amount of $^{166}$Ho. For complexation with DOTMP, 0.25 µL of the $6 \times 10^{-3}$ M $^{166}$HoCl$_3$ solution was mixed with 1 mL of a $6.04 \times 10^{-4}$ M $^{165}$HoCl3 solution. For complexation with EDTMP, 0.25 µL of the $6 \times 10^{-3}$ M $^{166}$HoCl$_3$ solution was mixed with 1 mL of a $4.84 \times 10^{-3}$ M $^{165}$HoCl$_3$ solution. These concentrations are chosen to fulfill the requirements of the DOTMP and EDTMP kits used for complexation.

Similarly, the radioactive $^{153}SmCl_3$ solution was mixed with non-radioactive $SmCl_3$ solutions to prepare solutions that would have only a tracer amount of $^{153}Sm$. For complexation with DOTMP, 0.25 µL of the $6×10^{-3}$ M $^{153}SmCl_3$ solution was mixed with 1 mL of a $6.06×10^{-4}$ M solution of non-radioactive Sm $(CH_3COO)_3$. For complexation with EDTMP, 0.25 µL of the $6×10^{-3}$ M $^{153}SmCl_3$ solution was mixed with 1 mL of a $4.84×10^{-3}$ M solution of non-radioactive Sm $(CH_3COO)_3$.

3. Preparation and Analysis of Complexes

Preparation of EDTMP complexes and DOTMP complexes was accomplished by the methods described in U.S. Pat. Nos. 4,898,724 and 4,976,950. Following preparation of the complexes, the percentage of complexation was determined. This was accomplished by placing an aliquot of the complexation solution onto a column of swollen Sephadex C-15 cation resin and eluting with a 4:1 physiologic saline: concentrated ammonium hydroxide solution. Percentage complexation can then be determined by comparison of the counts from non-complexed metal left on the column to the total of counts from the non-complexed metal on the column and the complexed metal in the eluted solution.

4. Biodistribution Studies

Rat biodistribution studies were done on Male Sprague-Dawley rats weighing 180–200 g that had been acclimated for approximately one week prior to this study. Four test complexes were used, Ho-DOTMP (Example 3), Ho-EDTMP (Example 4), Sm-DOTMP (Example 5) and Sm-EDTMP (Example 6). The rats were placed in a restraining cage that afforded accessibility to the left hind leg and tail. Prior to injection a tie wrap tourniquet was placed on the left hind femur above the knee to restrict blood flow. The amount of pressure induced by the tourniquet was standardized by using a tie wrap gun and was sufficient to stop arterial flow. Three rats per complex each received a 100.0 µL intravenous injection in a lateral tail vein. The tourniquets were allowed to remain in place for 5, 10 or 20 minutes post injection and were then removed. The rats were then watched for two hours, the usual biodistribution period used to allow excretion of all radioactive complexes not bound to tissue. The rats were then sacrificed for removal of tibias. The number of radioactive counts were then determined and compared to the average of number of counts of three 100.0 µL standards of the same material that was injected. Several additional tissues (femur, injection site, liver, kidney, spleen, muscle, and blood) were collected and counted for rats that had the 20 minutes restricted blood flow to check for expected renal excretion of radioactive complexes.

B. Results

Of the tissues checked, only the bone had significant radioactive counts present. This indicates normal clearance of the complexes not bound to bone and stability of the metal complexes.

Tables 1 and 2 show data as percent dose of administered radioactivity per gram of tissue. This reflects the concentration of the radioactive complex in the bone. Table 1 combines the data on the radioactivity found in the tibias of the rats from Examples 3 to 6 for each of the three times of tourniquet placement. Table 2 combines the data on the radioactivity found in the femurs of the rats from Examples 3 to 6 for the tourniquets applied for 20 minutes. The degree of "protection" of the bone by the tourniquet can be seen by comparison of the radioactivity in the bones on the left side ("protected" by the tourniquet for the time specified) as compared to the corresponding bones on the right side (fully exposed to the systemic, intravenous dose). Table 3 shows this comparison as the percentage of the concentration of radioactive complex in the unprotected bone found in the corresponding protected bone.

The 20 minute animal data indicates high uptake of the radioactivity in bone with very little activity remaining in any soft tissue. Examination of Table 3 reveals that the tibias behind the tourniquets concentrated less of the radioactive bone-seeking agents than the corresponding tibias regardless of the length of time the tourniquet remained in place or the specific complex used. However, leaving the tourniquets in place for 20 minutes provided much better protection than shorter time periods. Examples 3, 4, and 5 all showed only 20% to 25% of the unprotected radioactivity concentration in the protected tibias while Example 6 (Sm-EDTMP) was less effective at 36%. The tourniquet was placed in the middle of the left femur. Thus the femur was only partially protected from the systemically administered radioactive bone-seeking agents. Table 3 shows that Examples 3 and 5 (Ho-DOTMP and Sm-DOTMP) were still able to keep the concentration of radioactivity in the 20% to 25% range in the femur. Examples 4 and 6 (Ho-EDTMP and Sm-EDTMP) were only able to lower the concentration of radioactivity to 40% to 50% of unprotected concentration in the femur.

TABLE 1

Tibial Percentage Dose per Gram for Examples 3 to 6

|  | 5 minute | 10 minute | 20 minute |
|---|---|---|---|
| Ho-DOTMP Right Tibia | 7.06 | 7.52 | 6.39 |
| Ho-DOTMP Left Tibia | 3.19 | 3.41 | 1.35 |
| Ho-EDTMP Right Tibia | 1.60 | 6.95 | 5.33 |
| Ho-EDTMP Left Tibia | 1.35 | 3.49 | 1.25 |
| Sm-DOTMP Right Tibia | 7.91 | 6.79 | 8.34 |
| Sm-DOTMP Left Tibia | 4.82 | 3.38 | 2.06 |
| Sm-EDTMP Right Tibia | 6.73 | 6.17 | 5.73 |
| Sm-EDTMP Left Tibia | 5.33 | 2.56 | 2.04 |

TABLE 2

Femoral Percentage Dose per Gram for Examples 3 to 6

|  | 20 minute |
|---|---|
| Ho-DOTMP Right Femur | 5.59 |
| Ho-DOTMP Left Femur | 1.33 |
| Ho-EDTMP Right Femur | 4.31 |
| Ho-EDTMP Left Femur | 2.33 |
| Sm-DOTMP Right Femur | 6.46 |
| Sm-DOTMP Left Femur | 1.40 |
| Sm-EDTMP Right Femur | 5.44 |
| Sm-EDTMP Left Femur | 2.05 |

TABLE 3

Dose per Gram in Left Leg as a Percentage of Dose per Gram in Right Leg for Examples 3 to 6

|  | 5 minute | 10 minute | 20 minute |
|---|---|---|---|
| Ho-DOTMP Tibia | 45 | 45 | 21 |
| Ho-EDTMP Tibia | 84 | 50 | 23 |
| Sm-DOTMP Tibia | 61 | 50 | 25 |
| Sm-EDTMP Tibia | 79 | 41 | 36 |
| Ho-DOTMP Femur |  |  | 24 |
| Ho-EDTMP Femur |  |  | 54 |
| Sm-DOTMP Femur |  |  | 22 |
| Sm-EDTMP Femur |  |  | 38 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A method for the treatment of osteomyelitis comprising:
   intramuscularly administering a composition comprising a radionuclide to a subject suffering from osteomyelitis under conditions such that said osteomyelitis is reduced, wherein said osteomyelitis affects a bone located in a limb; and
   applying a tourniquet to the limb or limbs affected by osteomyelitis under conditions such that arterial blood flow to said limb or limbs is obstructed before administering the composition such that some portion of the bone marrow of said subject is protected from ablation.

2. A method for the treatment of osteomyelitis comprising:
   locally administering a composition comprising a radionuclide to a subject suffering from osteomyclitis at a particular site of infection under conditions such that said osteomyelitis is reduced, wherein said particular site of infection is a bone located in a limb; and
   applying tourniquet to the limb or limbs affected by osteomyelitis under conditions such that arterial blood flow to said limb or limbs is obstructed before administering the composition such that some portion of the bone marrow of said subject is protected from ablation.

3. A method for the treatment of osteomyelitis comprising:
   a) applying a tourniquet to a subject suffering from osteomyelitis; and
   b) administering a composition comprising a radionuclide to the subject under conditions such that the osteomyelitis is reduced.

4. The method of claim 3 wherein the radionuclide is selected from the group consisting of Arsenic-77, Molybdenum-99, Rhodium-105, Lutetium-177, Cadmium-115, Antimony-122, Promethium-149, Osmium-193, Gold-198, Thorium-200, Samarium-153, Yttrium-90, Gadolinium-159, Rhenium-186, Rhenium-188, Holmium-166, Tin-117, Indium(In)-115, Dysprosium(Dy)-165, Lanthanum(La)-140, Ytterbium(Yb)-175, Scandium (Sc) 47, Actinium-225, Bismuth-212, and Bismuth-213.

5. The method of claim 3 wherein the composition further comprises a ligand selected from the group consisting of ethylenediaminetetramethylenephosphonicacid, diethylenetriaminepentamethylenephosphonic acid, hydroxyethylethylenediaminetrimethylenephosphonic acid, nitrilo-trimethylenephosphonic acid, tris(2-aminoethyl) aminehexamethylenephosphonic acid, methylene diphosphonate, hydroxymethylenediphosphonate, hydroxyethylidene diphosphonate, and ethane-1-hydroxy-1,1-diphosphonic acid.

6. The method according to claim 1, wherein the radionuclide is selected from the group consisting of Arsenic-77, Molybdenum-99, Rhodium-105, Lutetium-177, Cadmium-115, Antimony-122, Promethium-149, Osmium-193, Gold-198, Thorium-200, Samarium-153, Yttrium-90, Gadolinium-159, Rhenium-186, Rhenium-188, Holmium-166, Tin-117, Indium(In)-115, Dysprosium(Dy)-165, Lanthanum (La)-140, Ytterbium(Yb)-175, Scandium (Sc)47, Actinium-225, Bismuth-212, and Bismuth-213.

7. The method of claim 1 wherein the composition further comprises a ligand selected from the group consisting of ethylenediaminetetramethylenephosphonicacid, diethylenetriaminepentamethylenephosphonic acid, hydroxyethylethylenediaminetrimethylenephosphonic acid, nitrilo-trimethylenephosphonic acid, tris(2-aminoethyl) aminehexamethylenephosphonic acid, methylene diphosphonate, hydroxymethylenediphosphonate, hydroxyethylidene diphosphonate, and ethane-1-hydroxy-1,1-diphosphonic acid.

* * * * *